US012721958B2

(12) United States Patent
Friend et al.

(10) Patent No.: US 12,721,958 B2
(45) Date of Patent: Sep. 1, 2026

(54) STEAM INHALER DEVICE

(71) Applicant: MICHAEL TODD BEAUTY LP, Port St. Lucie, FL (US)

(72) Inventors: Michael Friend, Port St. Lucie, FL (US); Xu Neng Fei, Ningbo (CN)

(73) Assignee: Michael Todd Beauty LP, Port St. Lucie, FL (US)

( * ) Notice: Subject to any disclaimer, the term of this patent is extended or adjusted under 35 U.S.C. 154(b) by 0 days.

(21) Appl. No.: 19/422,548

(22) Filed: Dec. 17, 2025

(65) Prior Publication Data

US 2026/0166238 A1 Jun. 18, 2026

Related U.S. Application Data

(60) Provisional application No. 63/735,408, filed on Dec. 18, 2024.

(51) Int. Cl.

| | |
|---|---|
| ***A61M 11/04*** | (2006.01) |
| ***A61M 11/02*** | (2006.01) |
| ***A61M 15/00*** | (2006.01) |

(52) U.S. Cl.

CPC ........... *A61M 11/042* (2014.02); *A61M 11/02* (2013.01); *A61M 15/0001* (2014.02); *A61M 2202/0007* (2013.01); *A61M 2202/02* (2013.01); *A61M 2202/04* (2013.01); *A61M 2205/3368* (2013.01); *A61M 2205/3653* (2013.01);

(Continued)

(58) Field of Classification Search

CPC .......................... A61M 11/042; A61M 11/02; A61M 15/0001; A61M 2202/0007; A61M 2202/02; A61M 2202/04; A61M 2205/3368; A61M 2205/3653; A61M 2210/0606; A61M 2210/0618; A61M 2210/0625; A62B 9/00–003;

(Continued)

(56) References Cited

U.S. PATENT DOCUMENTS

| | | | | |
|---|---|---|---|---|
| 4,300,556 A | 11/1981 | Ochi et al. | | |
| 6,842,918 B2 * | 1/2005 | Fung | A61H 33/12 | 4/537 |

(Continued)

FOREIGN PATENT DOCUMENTS

| | | | | |
|---|---|---|---|---|
| GB | 2487401 A | 7/2012 | | |
| WO | WO-2005079898 A2 * | 9/2005 | A61M 16/16 |
| WO | WO-2018009871 A1 * | 1/2018 | A61M 3/0287 |

OTHER PUBLICATIONS

WO2005079898A2 Description Machine Translation Accessed 20260325 (Year: 2026).*

*Primary Examiner* — Elliot S Ruddie

(74) *Attorney, Agent, or Firm* — Philip E. Levy; Eckert Seamans Cherin & Mellott, LLC

(57) ABSTRACT

A steam inhaler device includes a housing, a mask, a reservoir having a first portion provided within the housing and a second portion protruding from the housing, a heating mechanism for generating stream, and a funnel member for delivering the water to the reservoir, wherein the funnel member includes a stem portion structured to be received within the second portion through the opening. Also, a fan may be provided within the housing that is structured to pull air in through and air intake and push the air to an area adjacent to a wall within the and push a mixture of the air and the steam into a conduit coupled to the mask.

22 Claims, 11 Drawing Sheets

(52) U.S. Cl.
CPC ............... *A61M 2210/0606* (2013.01); *A61M 2210/0618* (2013.01); *A61M 2210/0625* (2013.01)

(58) Field of Classification Search
CPC ........ B05B 17/00–085; F24F 2006/008; F24F 6/02–025
See application file for complete search history.

(56) References Cited

U.S. PATENT DOCUMENTS

| | | | | |
|---|---|---|---|---|
| 2004/0158919 | A1 | 8/2004 | Fung | |
| 2009/0324206 | A1 | 12/2009 | Young et al. | |
| 2011/0210458 | A1* | 9/2011 | Brodbeck | B01B 1/08 261/127 |
| 2017/0043106 | A1 | 2/2017 | Hyland et al. | |
| 2018/0078729 | A1 | 3/2018 | Niedermann et al. | |
| 2019/0231919 | A1 | 8/2019 | Mehnert et al. | |
| 2019/0351155 | A1 | 11/2019 | Montagnino et al. | |
| 2022/0001131 | A1 | 1/2022 | Kat | |
| 2023/0095052 | A1* | 3/2023 | Gundlach | A61M 11/042 128/203.27 |
| 2024/0173513 | A1 | 5/2024 | Niedermann et al. | |

* cited by examiner

STEAM INHALER DEVICE

CROSS-REFERENCE TO RELATED APPLICATIONS

This application claims priority to U.S. Provisional Patent Application Ser. No. 63/735,408, filed on Dec. 18, 2024, and titled "STEAM INHALER Device," the disclosure of which is incorporated herein by reference.

FIELD OF THE INVENTION

The disclosed concept relates generally to devices for the treatment of nasal, sinus, mouth and/or throat irritation, dryness, and/or congestion due to allergies and/or illness, and, in particular, to a handheld device for providing steam inhalation therapy for the treatment of nasal, sinus, mouth and/or throat irritation, dryness, and/or congestion.

BACKGROUND OF THE INVENTION

People often suffer from nasal, sinus, mouth and/or throat irritation, dryness, and/or congestion due to illnesses, such as a cold, a sinus infection or the flu, or allergies. For example, in the case of a cold, a sinus infection or the flu, the blood vessels of the sinuses typically become inflamed and irritated, which often leads to nasal congestion, also known as a stuffy nose. The same often happens in the case of allergies when the immune system reacts to a foreign substance, such as pollen or pet dander, that infiltrates the body.

Steam inhalation therapy is a widely used home remedy to relieve cold, flu and allergy symptoms. Steam inhalation therapy involves the direct inhalation of water vapor, also known as steam, into the airways of an individual. The warm, moist water vapor works by loosening or thinning the mucus in the nasal passages, throat, and lungs, allowing it to empty or pass more easily. The warm, moist water vapor also eases feelings of irritation and swollen blood vessels in, for example, the nasal passages or throat.

SUMMARY OF THE INVENTION

In one embodiment, the disclosed concept provides a steam inhaler device that includes a housing, a mask coupled to the housing, a reservoir for holding water, the reservoir having a first portion provided within the housing and a second portion protruding from the housing, the second portion including an opening, a heating mechanism provided within the housing for generating stream to be provided to the mask from the water held within the reservoir, and a funnel member for delivering the water to the reservoir, wherein the funnel member includes a stem portion structured to be received within the second portion through the opening.

In another embodiment, the disclosed concept provides a steam inhaler device that includes a housing, wherein a front side of the housing includes an air intake, a mask coupled to the housing and to a conduit provided within the housing, a reservoir for holding water, a wall coupled to a top side of the reservoir adjacent an opening provided in the reservoir, a heating mechanism provided within the housing for generating stream to be provided to the mask from the water held within the reservoir, wherein the heating mechanism is structured to cause the steam generated from the water in the reservoir to collect in an area adjacent to the wall, and a fan provided within the housing, wherein the fan is structured to pull air in through the air intake and push the air to the area adjacent to the wall and push a mixture of the air and the steam into the conduit and to the mask.

BRIEF DESCRIPTION OF THE DRAWINGS

A full understanding of the invention can be gained from the following description of the preferred embodiments when read in conjunction with the accompanying drawings in which.

DETAILED DESCRIPTION

Figure 1:
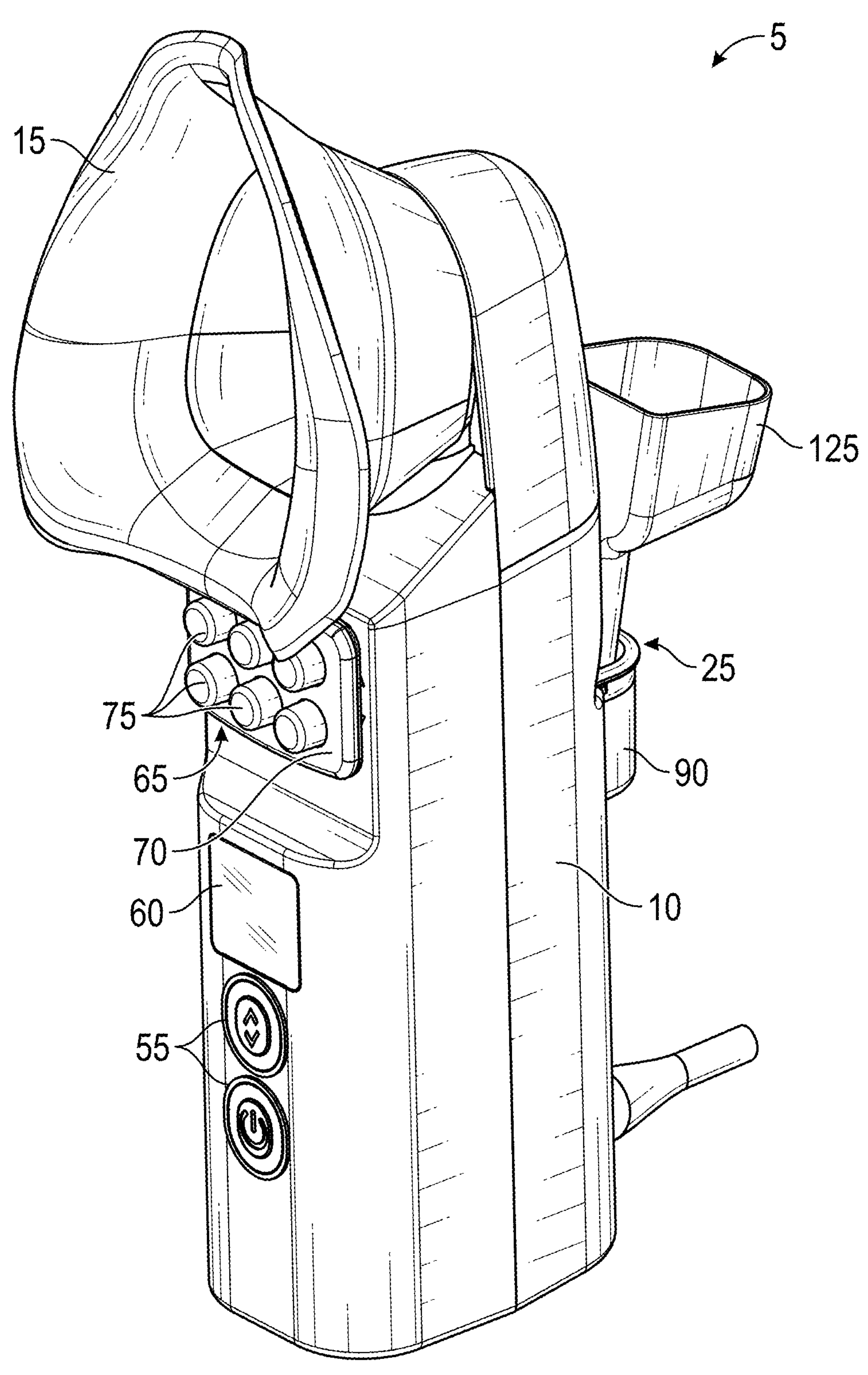
FIGS. 1-5 are front isometric, rear isometric, front elevational, side elevational, and rear elevation views, respectively, of a steam inhaler device according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the disclosed concept. It will be evident, however, that the disclosed concept can be practiced without these specific details without departing from the spirit and scope of this innovation.

FIGS. 1-5 are front isometric, rear isometric, front elevational, side elevational, and rear elevation views, respectively, of a handheld steam inhaler device 5 for delivering steam and/or purified air to the airways of a user for relieving cold, flu and/or allergy symptoms according to an exemplary embodiment of the disclosed concept. As described in detailed herein, steam inhaler device 5 includes a refillable water reservoir for holding sterile water that is to be turned into steam, which is then delivered to the user's airways by way of a mask. In addition, steam inhaler device 5 includes an internal rechargeable battery that enables steam inhaler device 5 to operate in a handheld, cordless manner when the battery is charged.

Referring to FIGS. 1-5, steam inhaler device 5 includes a main housing 10 and a latex-free mask 15 that is coupled to the top end of main housing 10. Mask 15 is shaped to cover the user's nose and mouth while steam inhaler device 5 is in use by creating a seal against the user's face. Housing 10 includes an internal reservoir 20, shown in FIGS. 6, 7, and 8, and described in more detail herein, for receiving and holding sterile water that is to be converted to steam. A filling mechanism 25, described in more detail herein, for filling reservoir 20 with sterile water is provided on the outside of housing.

Figure 8:
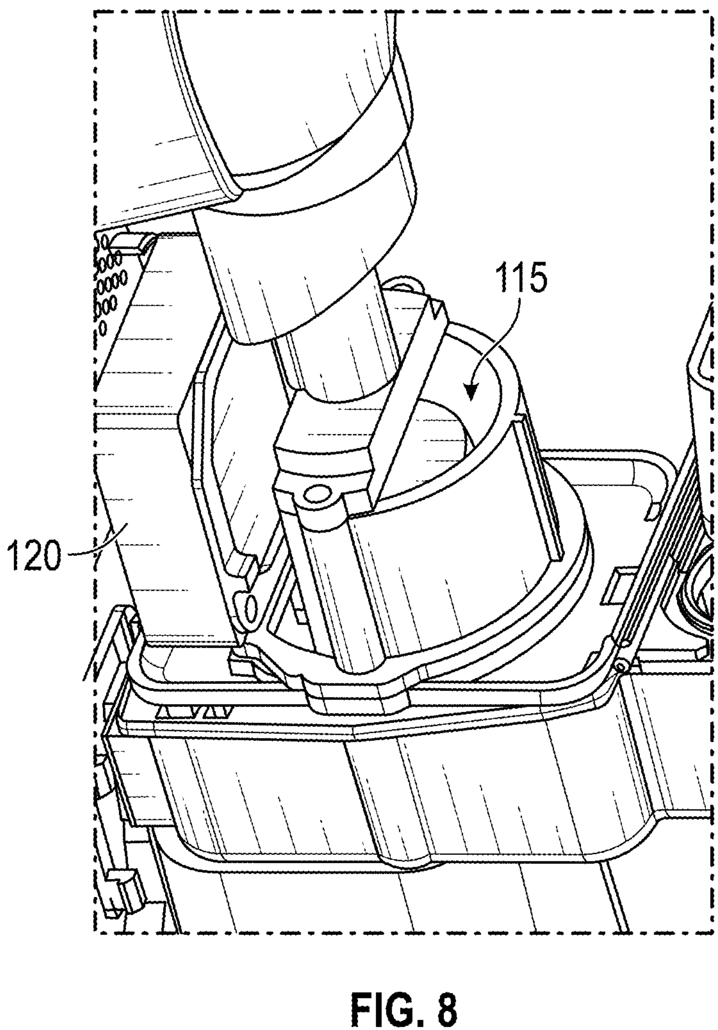
FIG. 8 shows a partially assembled version of the steam inhaler device of FIGS. 1-5 according to an exemplary embodiment of the disclosed concept.
Figure 9:
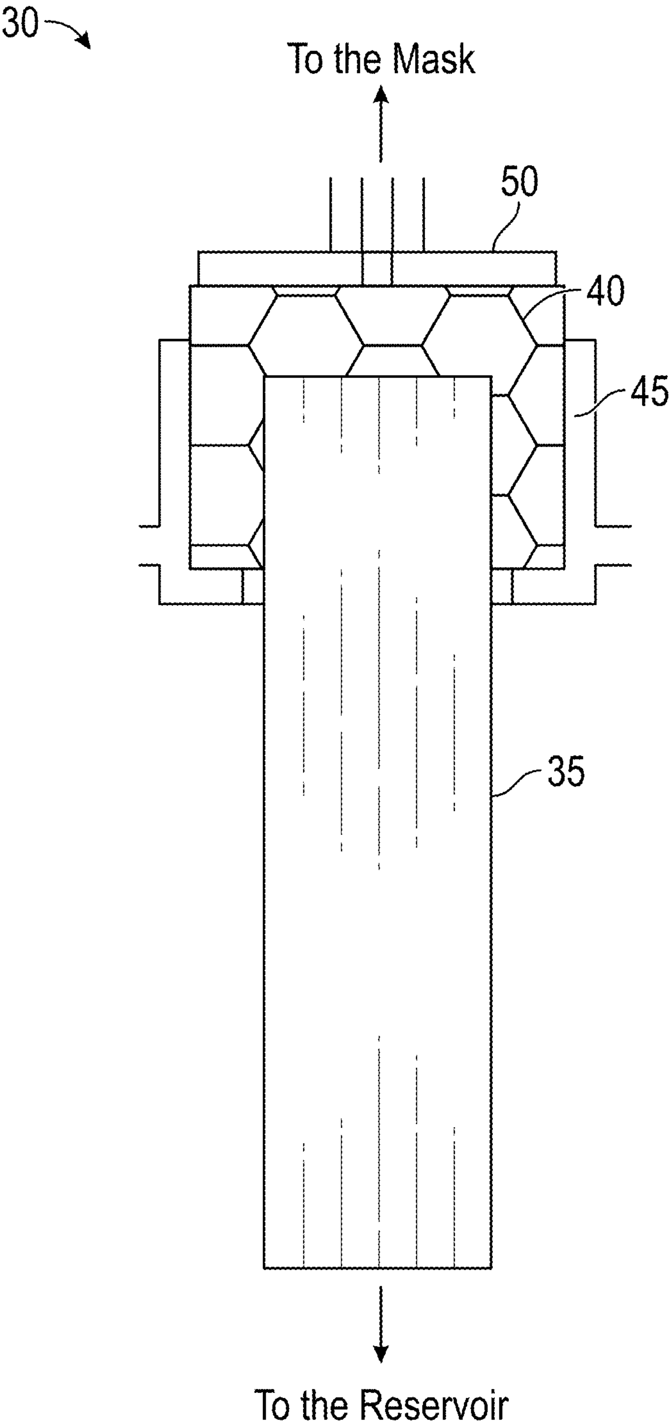
FIG. 9 is a schematic diagram of a heating mechanism that forms a part of the steam inhaler device of FIGS. 1-5 according to an exemplary embodiment of the disclosed concept.

Housing 10 includes and houses an internal heating mechanism 30, shown schematically in FIG. 9, for heating the sterile water contained in reservoir 20 to produce the steam that is provided to mask 15. In particular, in the exemplary embodiment, heating mechanism 30 comprises a capillary force vaporizer for instant steam generation. As is well known, capillary force vaporizers generate pressurized vapor from unpressurized liquid by providing the liquid to a capillary member (which is a porous member such as a ceramic) and applying heat to the capillary member to transform the liquid to a vapor state. As seen in FIG. 9, the capillary force vaporizer of the exemplary embodiment includes a cotton wick 35, a silicon carbide porous member 40 coupled to the top end of cotton wick 35, a sealing member 45 surrounding porous member 40, and a ceramic heating element 50 (coupled to a power source within housing 10, not shown) positioned on top of porous member 40. The bottom end of cotton wick 35 is positioned within reservoir 20 and is structured to transport sterile water from reservoir 20 to porous member 40. The sterile water in porous member 40 is heated by ceramic heating element 50 to produce stream, which is then delivered to mask 15 through an internal conduit 145 (see FIG. 8 described herein).

Steam inhaler device 5 may be powered on and off by way of a number of buttons 55 on the front face of housing 10. Also, the temperature of heating element 50 is adjustable by way of one or more of the buttons 55 to enable control of the temperature of the steam that is delivered to mask 15. An LCD display 60 is provided on the front face of housing 10 to show information about the current operational state of steam inhaler device 5, such as, without limitation, the current selected temperature level and current battery level.

In addition, the front face of housing 10 includes a cooling air intake that is in fluid communication with the inside of housing 10, and in particular a portion that collects the generated steam (described elsewhere herein) in order to enable ambient air to be drawn into housing 10 and mixed with the steam to create a humidified mist. A scent-pad 65 is structured to be selectively coupled to the cooling air intake (over and covering the air intake as shown in FIGS. 1-4). Scent-pad 65 includes a sent source material that enables ambient air to be mixed with the sent source material to produce a scented flow of air into housing 10. In particular, scent-pad 65 includes a frame member 70 that holds a plurality of round/dome shaped scent receptables 75 that hold a liquid or solid scent source material, such as a scented oil. In addition, in the exemplary embodiment, the air intake is coupled to an internal air filter/purifier (not shown), such as a HEPA grade filter, that is housed within housing 10 to purify the air (scented or unscented) that is received through the cooling air intake. In addition, a fan (see fan 120 in FIG. 8 described below) is provided in housing 10 to draw ambient air into housing 10 through the cooling air intake.

Figure 2:
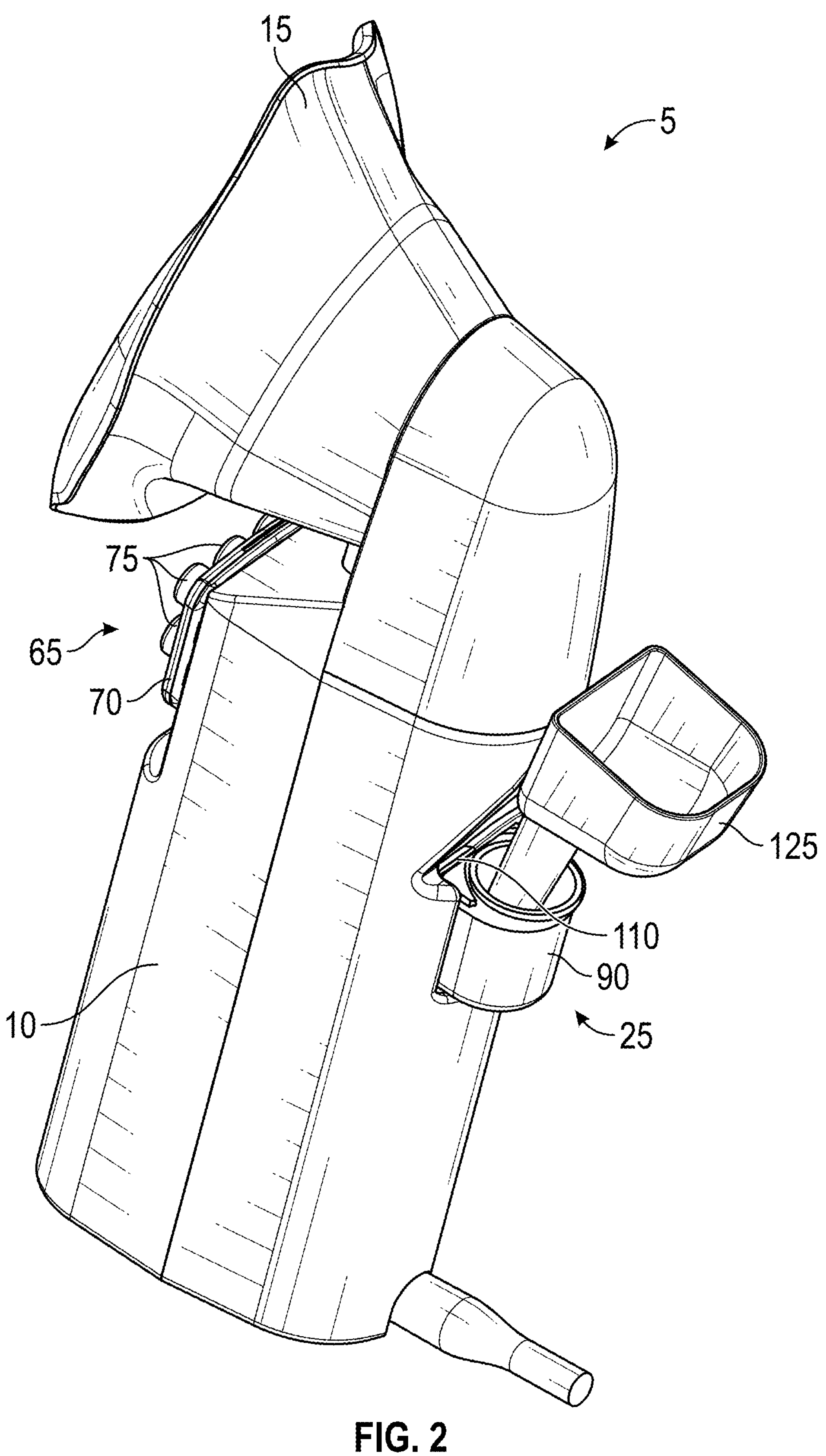
Figure 3:
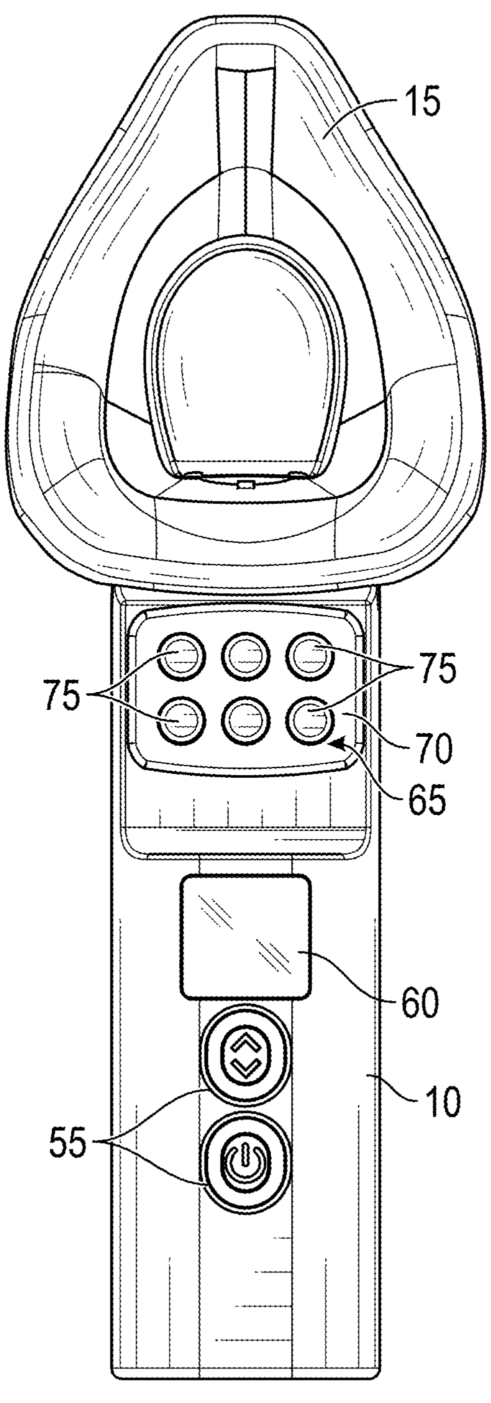
Figure 4:
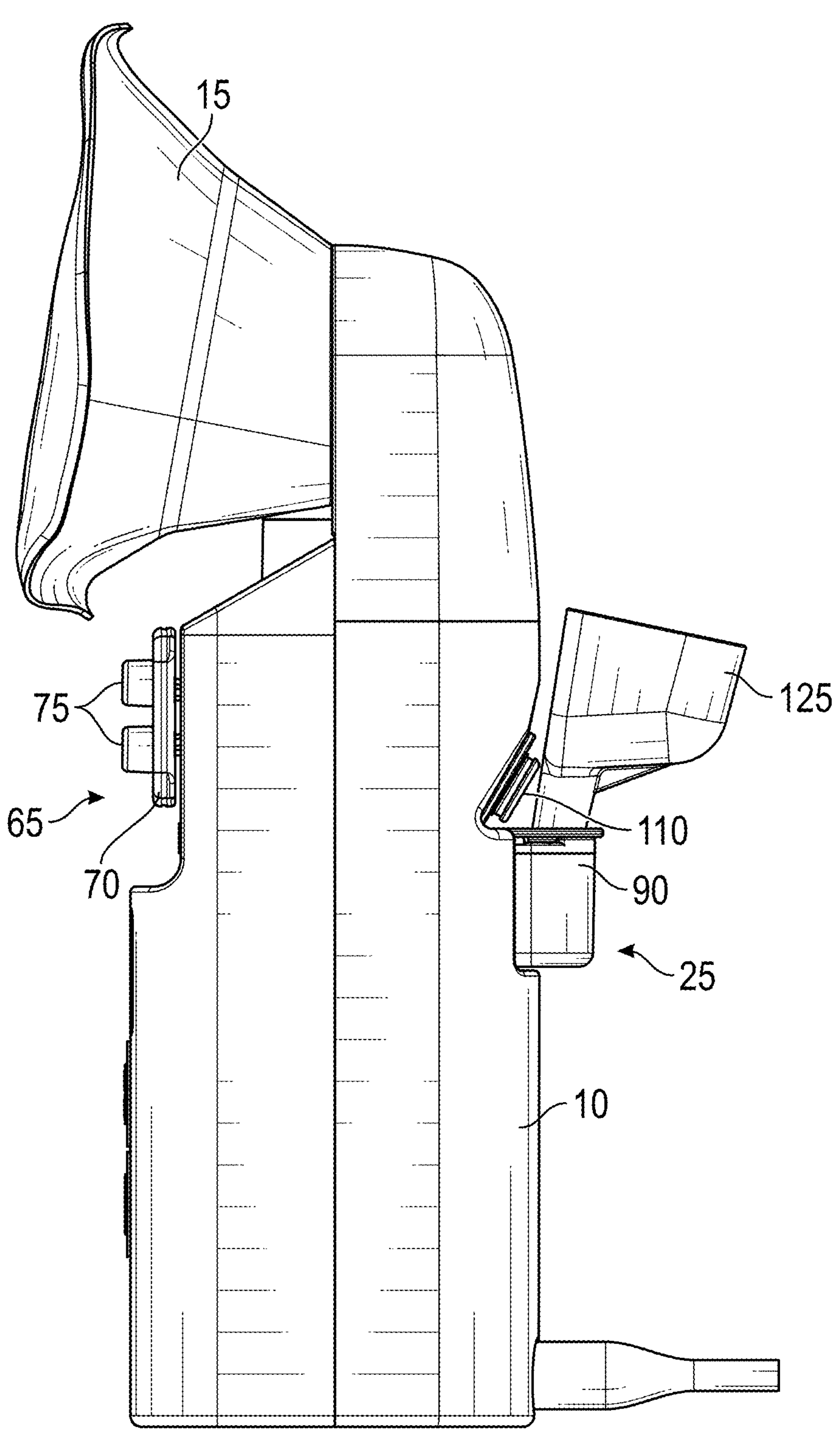
Figure 5:
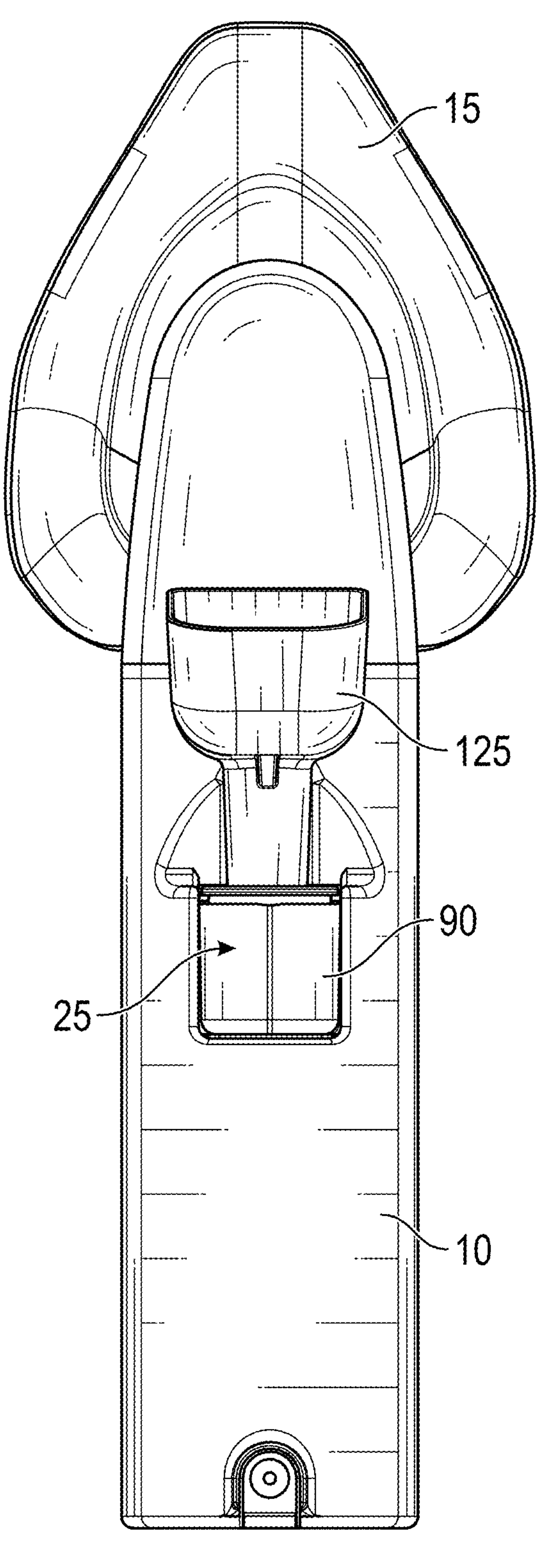
Figure 6:
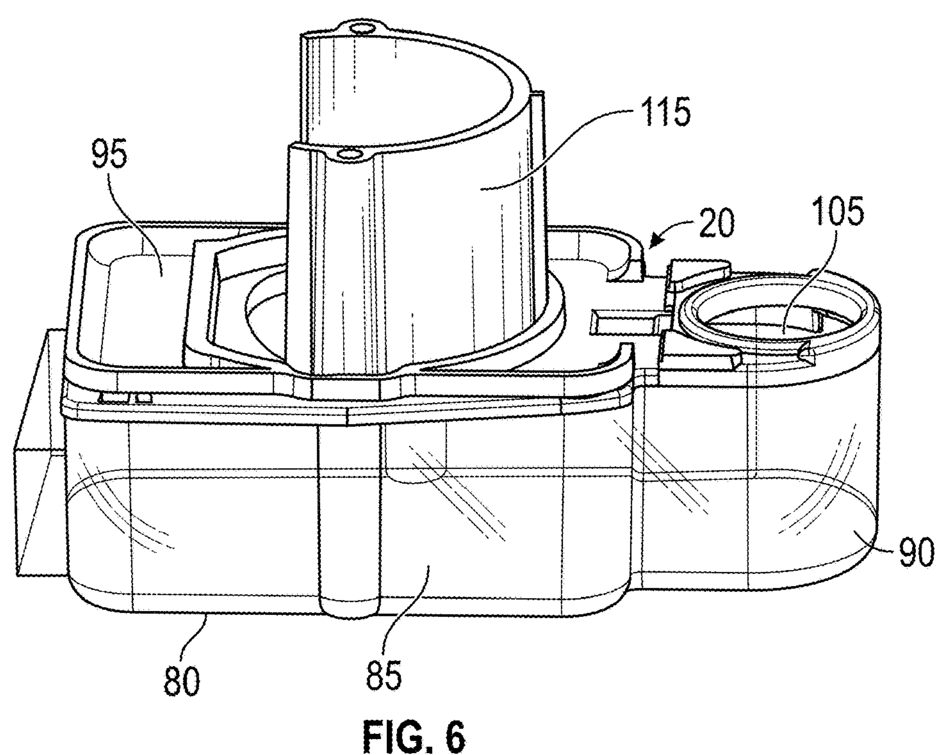
FIGS. 6 and 7 are isometric views of a reservoir for holding sterile water that forms a part of the steam inhaler device of FIGS. 1-5 according to an exemplary embodiment of the disclosed concept.
Figure 7:
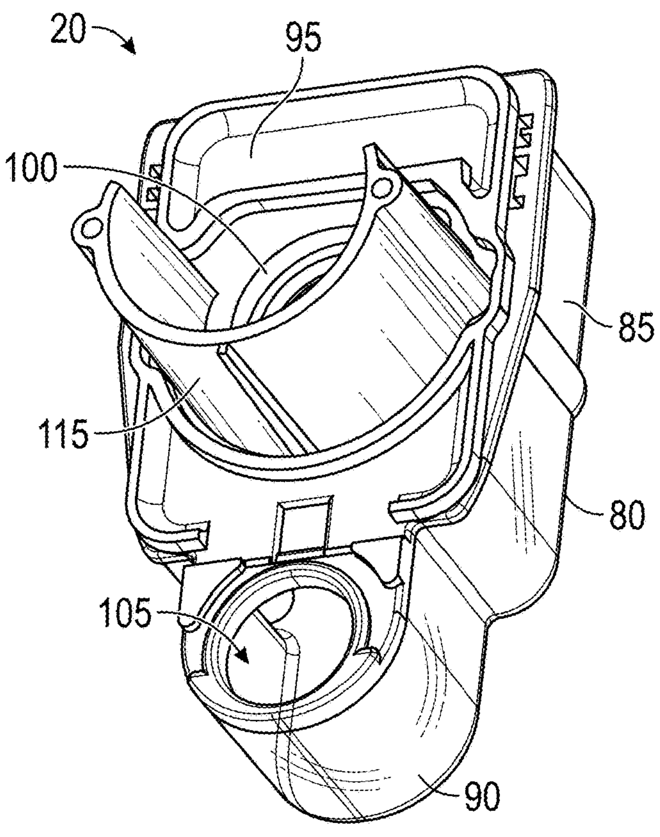

Referring to FIGS. 6 and 7, reservoir 20 includes a container member 80 having a main portion 85 and a protruding portion 90. A cover member 95 covers container member 80. Cover member 95 includes a first aperture 100 for providing direct access to main portion 85 and a second aperture 105 for providing direct access to protruding portion 90. In addition, as seen in FIGS. 2 and 4, a pivotable cover 110 is attached to cover member 95 for selectively covering second aperture 105 (for example when not filling reservoir 20 as described herein). Also, a semi-circular wall 115 is provided between first aperture 100 and second aperture 105. The purpose of wall 115 is described below.

When steam inhaler device 5 is assembled, reservoir 20 is provided in housing 10 in a manner wherein main portion 85 is contained entirely within housing 10 and protruding portion 90 protrudes from an opening provided in the back of housing 10 as shown in FIGS. 1, 2, 4 and 5. In this manner, protruding portion 90 forms part of filling mechanism 25, which is described in detail below. When so assembled, wick 35 of heating mechanism 30 is received through first aperture 100 so that it may be in contact with the sterile water held within container member 80.

FIG. 8 shows a view of steam inhaler device 5 in a partially assembled form. In this view, reservoir 20 and fan 120 can be seen in assembled form. When heating mechanism 30 operates, the generated steam/mist will gather and collect in the space adjacent to wall 115. Fan 120 functions to draw ambient air though the cooling air intake and toward wall 115, which assists to divert the flow of the air (mixed with the scent provided by scent-pad 65 as described herein) and steam to mask 15 through internal conduit 145. Wall 115 also functions as a mount for an internal temperature sensor 150.

Figure 10:
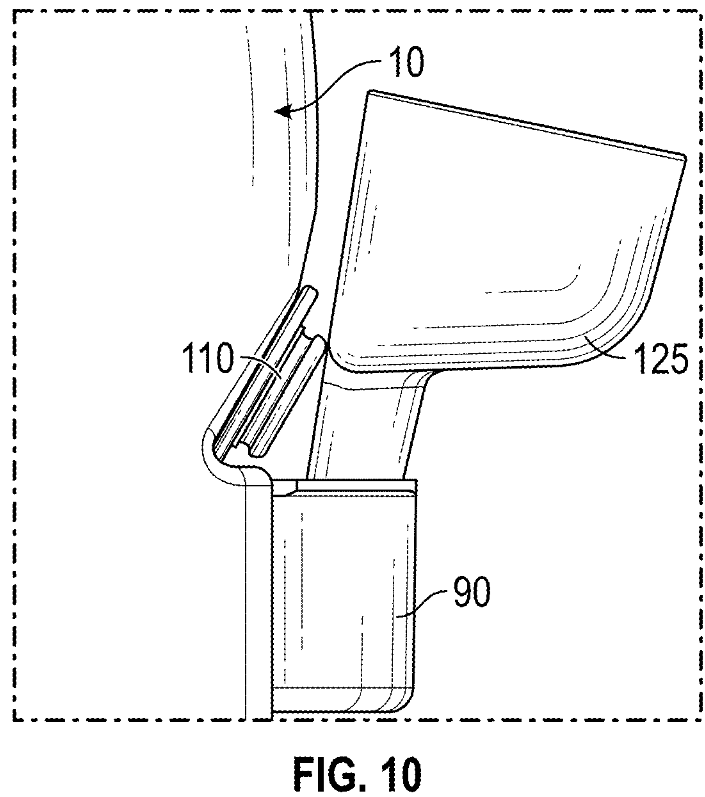
FIG. 10 is a focused side view of the steam inhaler device of FIGS. 1-5 according to an exemplary embodiment of the disclosed concept which shows the filling mechanism of the device.
Figure 11:
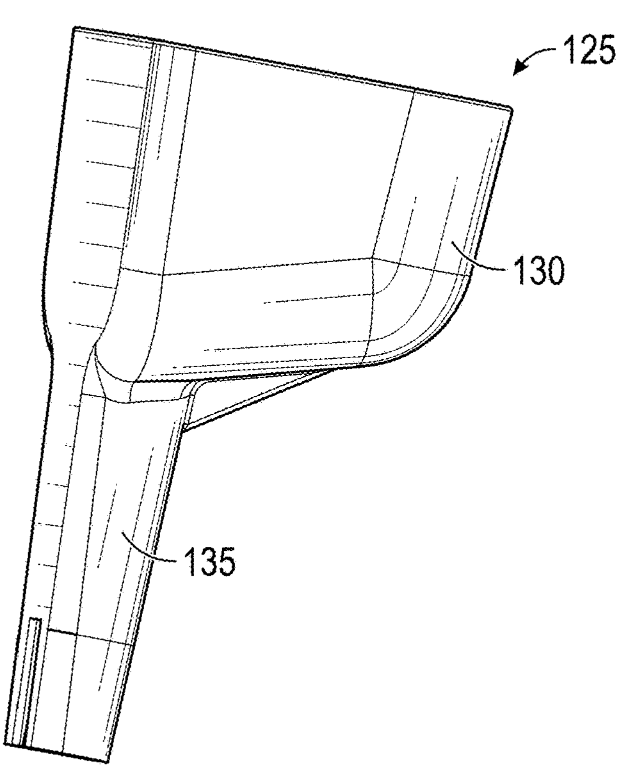
FIG. 11 is a side view.
Figure 12:
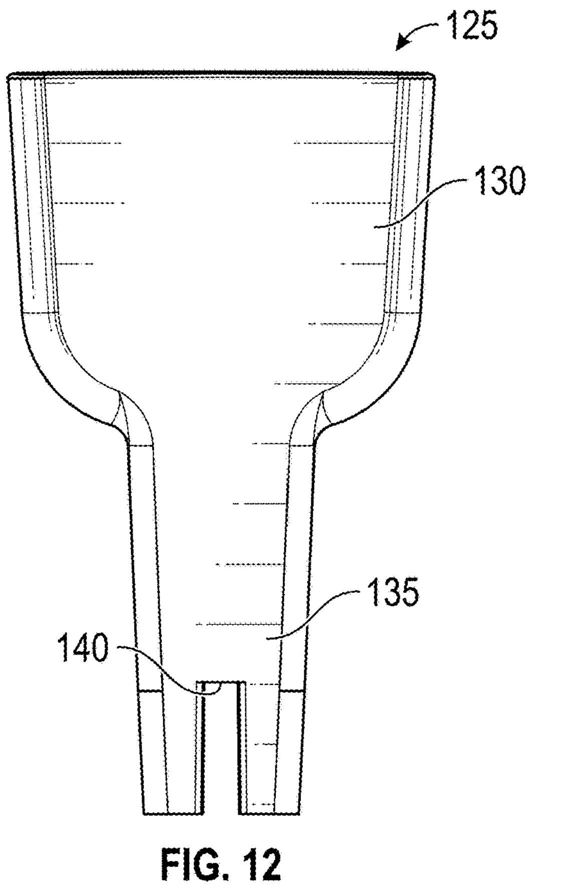
FIG. 12 is a front view.
Figure 13:
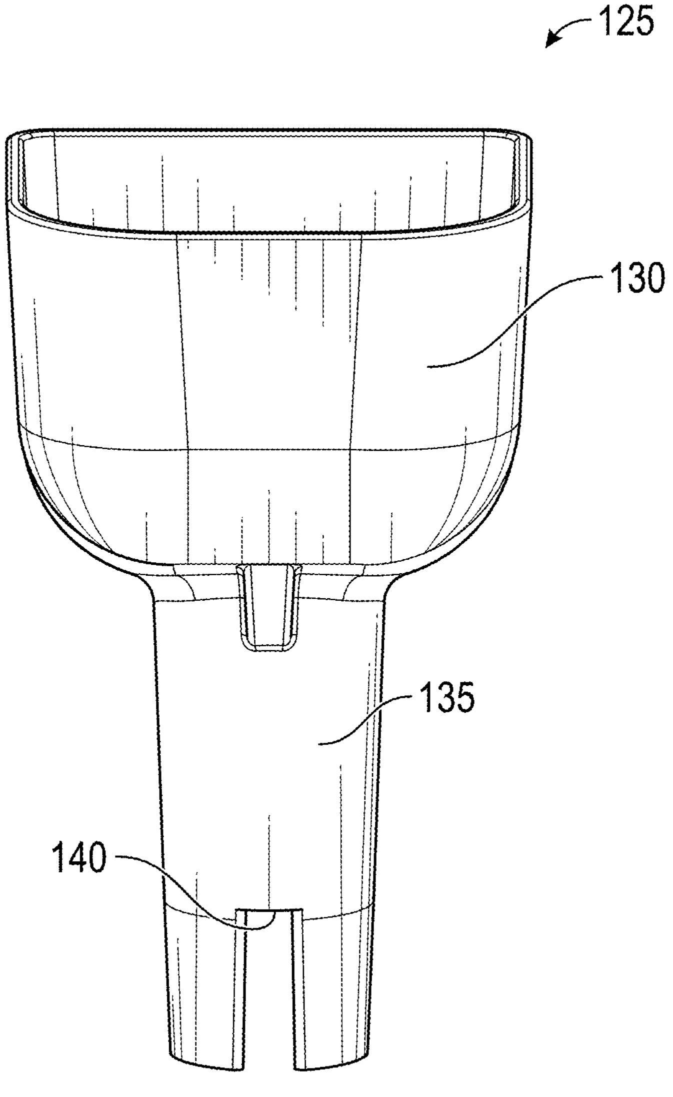
FIG. 13 is a rear view of a funnel member of the filling mechanism shown in FIG. 10.

A noted elsewhere herein, steam inhaler device 5 includes filling mechanism 25 provided on the outside of housing 10 for filling reservoir 20 with sterile water. Filling mechanism 25 includes protruding portion 90 that protrudes from an opening provided in the back of housing 10, pivotable cover 110, and a funnel member 125 that is structured to be received within protruding portion 90 through second aperture 105. Funnel member 125 facilitates the delivery of sterile water to reservoir 20 by the user. Filling mechanism 25 with funnel member 125 inserted into protruding portion 90 is shown in FIG. 10. In addition, FIG. 11 is a side view, FIG. 12 is a front view, and FIG. 13 is a rear view of funnel member 125 according to the exemplary embodiment of the disclosed concept. Funnel member 125 includes a top basin portion 130 for receiving the sterile water and a downwardly extending stem portion 135 for delivering the sterile water to the protruding portion 90. In the exemplary embodiment, stem portion 135 is offset from the center of basin portion 130. As seen in FIGS. 13 and 13, the front and back walls of the distal portion of stem portion 135 each include a cutout 140. Cutouts 140 facilitate the release of sterile water from stem portion 135 and into protruding portion 90 during the filling of reservoir 20.

In operation, the user fills reservoir 20 within housing 10 with sterile water using filling mechanism 25 as just described. The user then powers steam inhaler device 5 device on and steam is generated by heating mechanism 30 and delivered to mask 15 as described herein. In addition, the steam that is generated is mixed with unscented or scented air that is drawn in through the cooling air intake. As a result, a therapeutic warm mist is delivered to the user's airways through mask 115. The user is able to adjust the temperature of the steam using buttons 55 on the front face of housing 10. In addition, steam inhaler device 5 is able to be operated in an air purifier only mode wherein only purified air (scented or unscented) that is drawn into the cooling air intake through the filter is delivered to mask 15 (i.e., no steam is generated and delivered through mask 15).

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of disclosed concept which is to be given the full breadth of the claims appended and any and all equivalents thereof.

What is claimed is:

1. A steam inhaler device, comprising:
- a housing;
- a mask coupled to the housing;
- a reservoir for holding water, the reservoir having a first portion provided within the housing and a second portion protruding from the housing, the second portion including an opening;
- a heating mechanism provided within the housing for generating stream to be provided to the mask from the water held within the reservoir;
- a funnel member for delivering the water to the reservoir, wherein the funnel member includes a stem portion structured to be received within the second portion through the opening; and
- a fan provided within the housing, wherein the mask is coupled to a conduit provided within the housing, wherein a front side of the housing includes an air intake, wherein a wall is coupled to a top side of the first portion of the reservoir adjacent a hole provided in the first portion, wherein the heating mechanism is structured to cause the steam generated from the water in the reservoir to collect in an area adjacent to the wall, and wherein the fan is structured to pull air in through the air intake and push the air to the area adjacent to the wall and push a mixture of the air and the steam into the conduit and to the mask.

2. The steam inhaler according to claim 1, wherein the reservoir includes a pivotable cover for selectively covering the opening.

3. The steam inhaler according to claim 1, wherein the funnel member includes a basin portion coupled to the stem portion, wherein the stem portion is offset from a center of the basin portion.

4. The steam inhaler according to claim 1, wherein the heating mechanism comprises a capillary force vaporizer.

5. The steam inhaler according to claim 1, wherein the mask extends outwardly from a front side of the housing and the second portion protrudes from a rear side of the housing.

6. The steam inhaler according to claim 1, wherein the fan is positioned to push the air to the area adjacent to the wall in a first direction, wherein at least a portion of the conduit that receives the mixture of the air and the steam extends in a second direction that is perpendicular to the first direction.

7. The steam inhaler according to claim 6, wherein the air intake is provided in a housing wall of the housing provided on a front side of the housing wherein the housing wall extends in the second direction.

8. The steam inhaler according to claim 1, further comprising a temperature sensor directly connected to the wall.

9. The steam inhaler according to claim 1, wherein the wall is a semicircular wall.

10. The steam inhaler according to claim 1, further comprising a scent source coupled to the air intake.

11. The steam inhaler according to claim 10, wherein the scent source comprises a scent-pad having a frame and a plurality of receptables holding a scent material.

12. The steam inhaler according to claim 1, wherein the first portion of the reservoir has a generally rectangular cross-section and the second portion of the reservoir has a curved cross-section.

13. A steam inhaler device, comprising:
- a housing;
- a mask coupled to the housing;
- a reservoir for holding water, the reservoir having a first portion provided within the housing and a second portion protruding from the housing, the second portion including an opening;
- a heating mechanism provided within the housing for generating stream to be provided to the mask from the water held within the reservoir; and
- a funnel member for delivering the water to the reservoir, wherein the funnel member includes a stem portion structured to be received within the second portion through the opening, wherein the stem portion includes a first wall and a second wall, wherein a first cutout is provided in a distal end of the first wall and a second cutout is provided in a distal end of the second wall.

14. The steam inhaler according to claim 13, wherein the first wall is a front wall and the second wall is a rear wall opposite the front wall.

15. A steam inhaler device, comprising:
- a housing, wherein a front side of the housing includes an air intake;
- a mask coupled to the housing and to a conduit provided within the housing;
- a reservoir for holding water,
- a wall coupled to a top side of the reservoir adjacent an opening provided in the reservoir;
- a heating mechanism provided within the housing for generating steam to be provided to the mask from the water held within the reservoir, wherein the heating mechanism includes a heating element located between a bottom end of the conduit and the top side of the reservoir above the opening, wherein the heating element is positioned to enable the steam generated from the water in the reservoir to collect in an area adjacent to the wall; and
- a fan provided within the housing directly opposite and facing the wall, wherein the heating element is located between the fan and the wall, wherein the fan is structured to pull air in through the air intake and push the air to the area adjacent to the wall and push a mixture of the air and the steam into the conduit and to the mask.

16. The steam inhaler according to claim 15, wherein the fan is positioned to push the air to the area adjacent to the wall in a first direction, wherein at least a portion of the conduit that receives the mixture of the air and the steam extends in a second direction that is perpendicular to the first direction.

17. The steam inhaler according to claim 16, wherein the air intake is provided in a housing wall of the housing provided on the front side of the housing, wherein the housing wall extends in the second direction.

18. The steam inhaler according to claim 15, further comprising a temperature sensor directly connected to the wall.

19. The steam inhaler according to claim 15, wherein the wall is a semicircular wall.

20. The steam inhaler according to claim 15, further comprising a scent source coupled to the air intake.

21. The steam inhaler according to claim 20, wherein the scent source comprises a scent-pad having a frame and a plurality of receptables holding a scent material.

22. The steam inhaler according to claim 15, wherein the heating mechanism comprises a capillary force vaporizer including the heating element, a porous member and a wick, wherein the porous member is coupled to a top end of the wick, wherein a bottom end of the wick is received through the opening in the reservoir to enable the wick to transport the water from the reservoir to the porous member, and wherein the heating element is positioned on top of the porous member such that at least a portion of the porous member is located in between the wick and the heating element.

* * * * *